United States Patent [19]

Ludwig

[11] Patent Number: 5,056,744
[45] Date of Patent: Oct. 15, 1991

[54] SYRINGE BOTTLE SUPPORT APPARATUS

[76] Inventor: John G. Ludwig, 480 S. Arcadia Ave., Arcadia, Fla. 33821

[21] Appl. No.: 619,388

[22] Filed: Nov. 29, 1990

[51] Int. Cl.$^5$ ............................................. A61B 19/00
[52] U.S. Cl. .................................... 248/154; 248/313
[58] Field of Search ..................... 248/311.3, 154, 542, 248/105, 106, 109, 121, 146, 150, 176, 177, 187, 309.1, 311.2, 313, 316.1, 505; 604/411, 414, 403; 141/375; 222/181; 211/74

[56] References Cited

U.S. PATENT DOCUMENTS

| | | | |
|---|---|---|---|
| 2,028,694 | 1/1936 | Spinks | 248/110 |
| 2,201,257 | 5/1940 | Bell | 248/105 |
| 2,489,773 | 11/1949 | Hall | 248/105 |
| 2,677,372 | 5/1954 | Barnish, Jr. | 248/311.3 |
| 2,899,153 | 8/1959 | Parker | 248/694 |
| 3,762,673 | 10/1973 | Koslovsky | 248/154 |
| 3,982,716 | 9/1976 | Trees | 248/311.3 |
| 4,001,444 | 1/1977 | Clarke | 248/154 |
| 4,475,915 | 10/1984 | Sloane | 604/414 |
| 4,489,766 | 12/1984 | Montada | 141/375 |
| 4,557,451 | 12/1985 | Conway | 248/177 |

*Primary Examiner*—Ramon O. Ramirez
*Assistant Examiner*—Robert A. Olson
*Attorney, Agent, or Firm*—Leon Gilden

[57] ABSTRACT

An apparatus arranged to fixedly mount a syringe bottle in a downwardly angulated orientation, including a support member formed with a concave semi-cylindrical sleeve, with the sleeve mounting an elastomeric band selectively securable to a side of the sleeve for assembly of the bottle to the sleeve to permit access of the bottle in filling of a syringe therefrom. A modification of the invention includes illumination structure to enhance visibility of the organization in use.

2 Claims, 4 Drawing Sheets

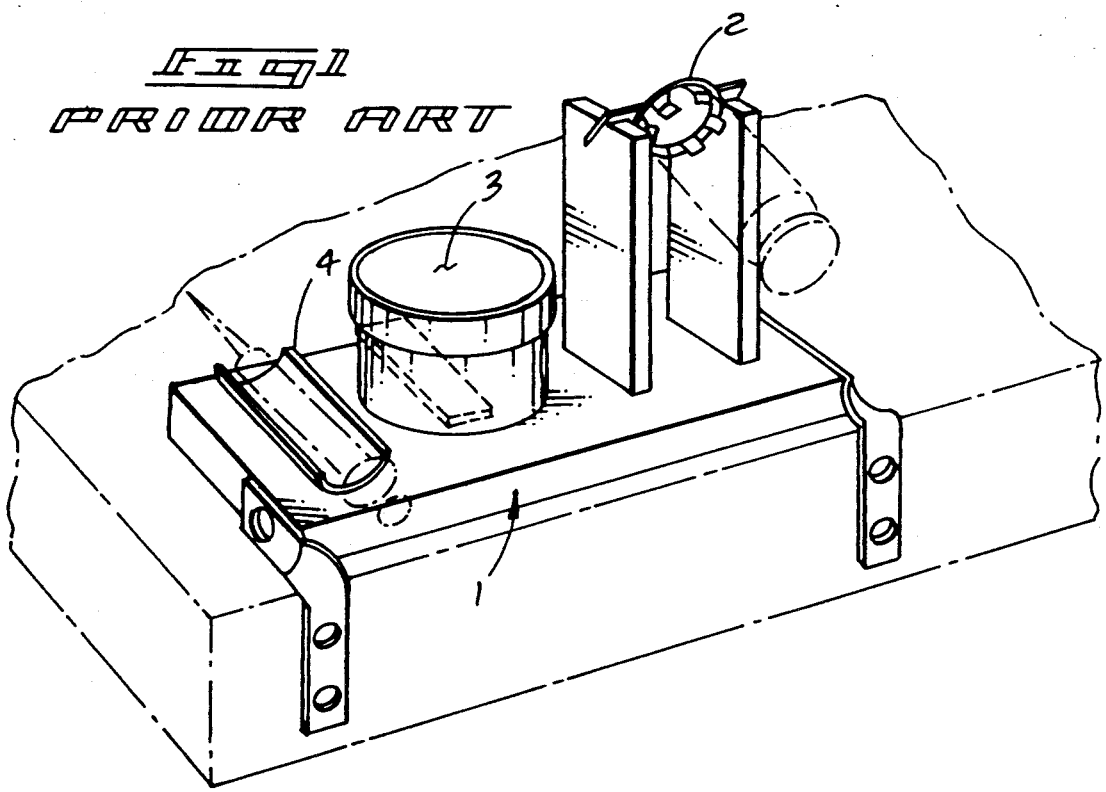
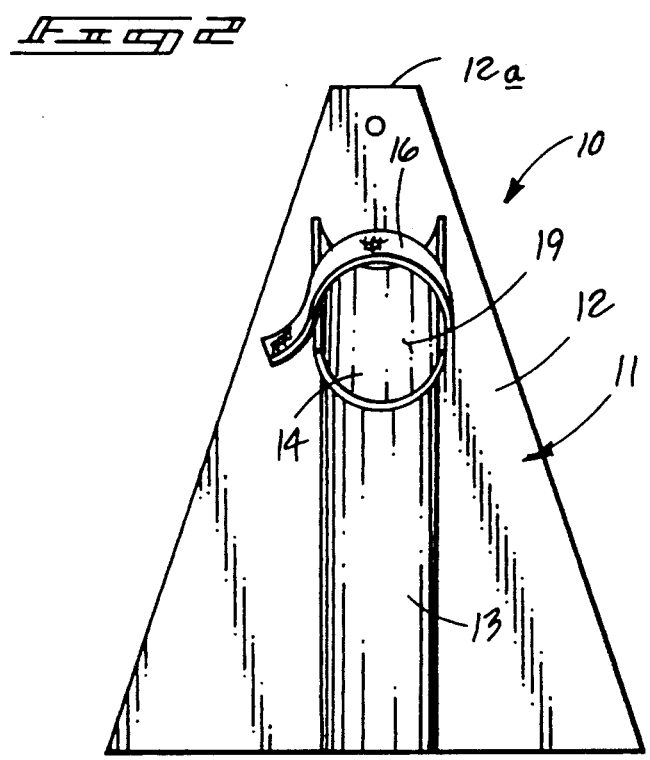

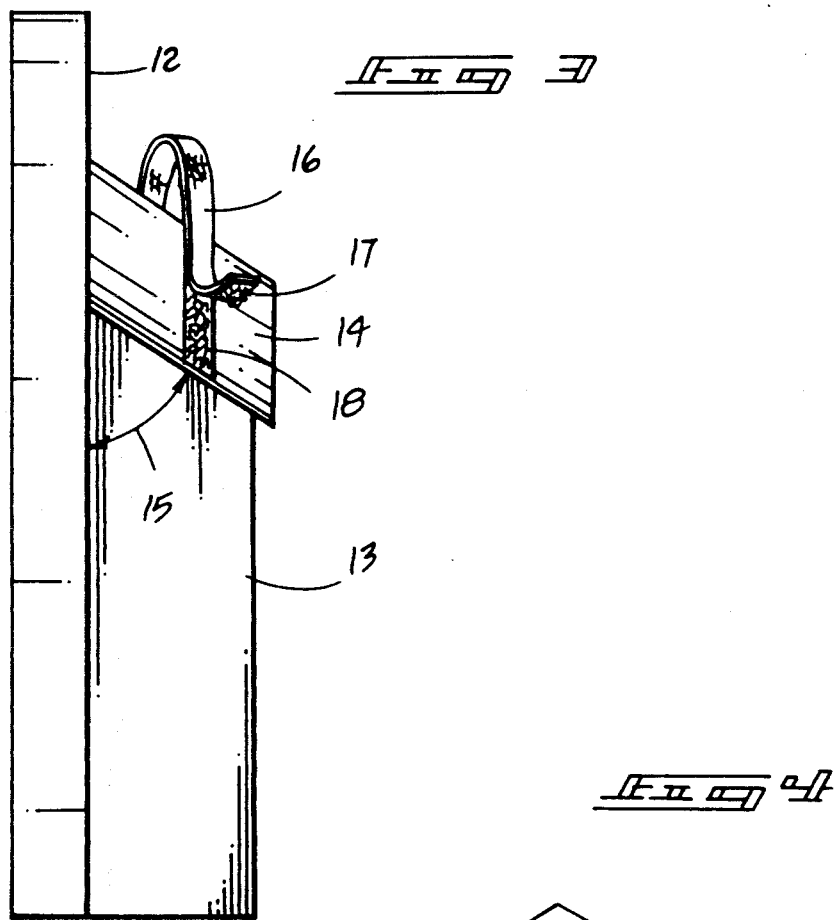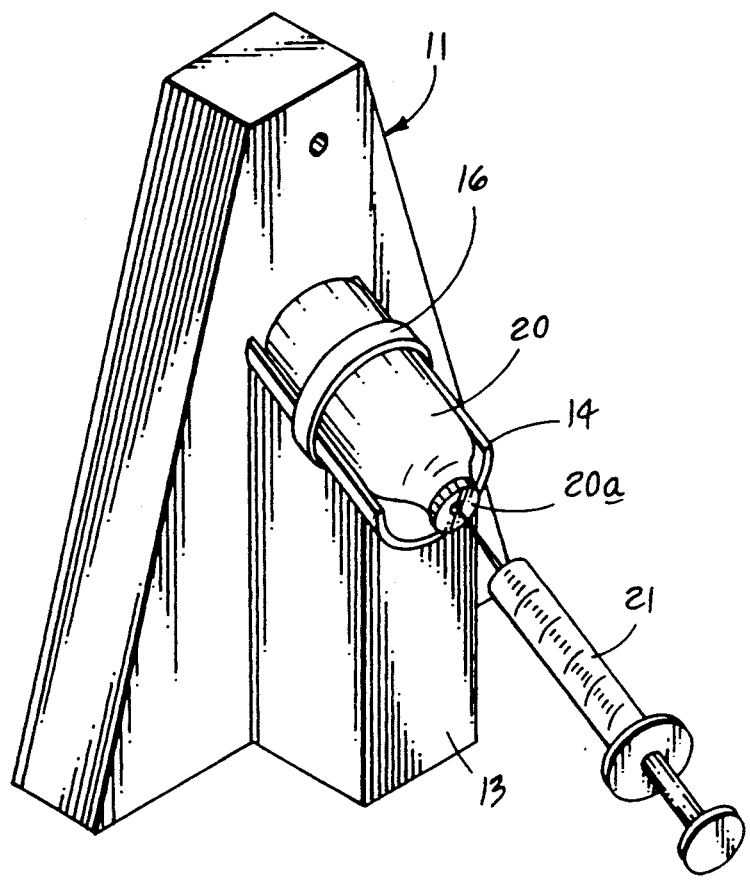

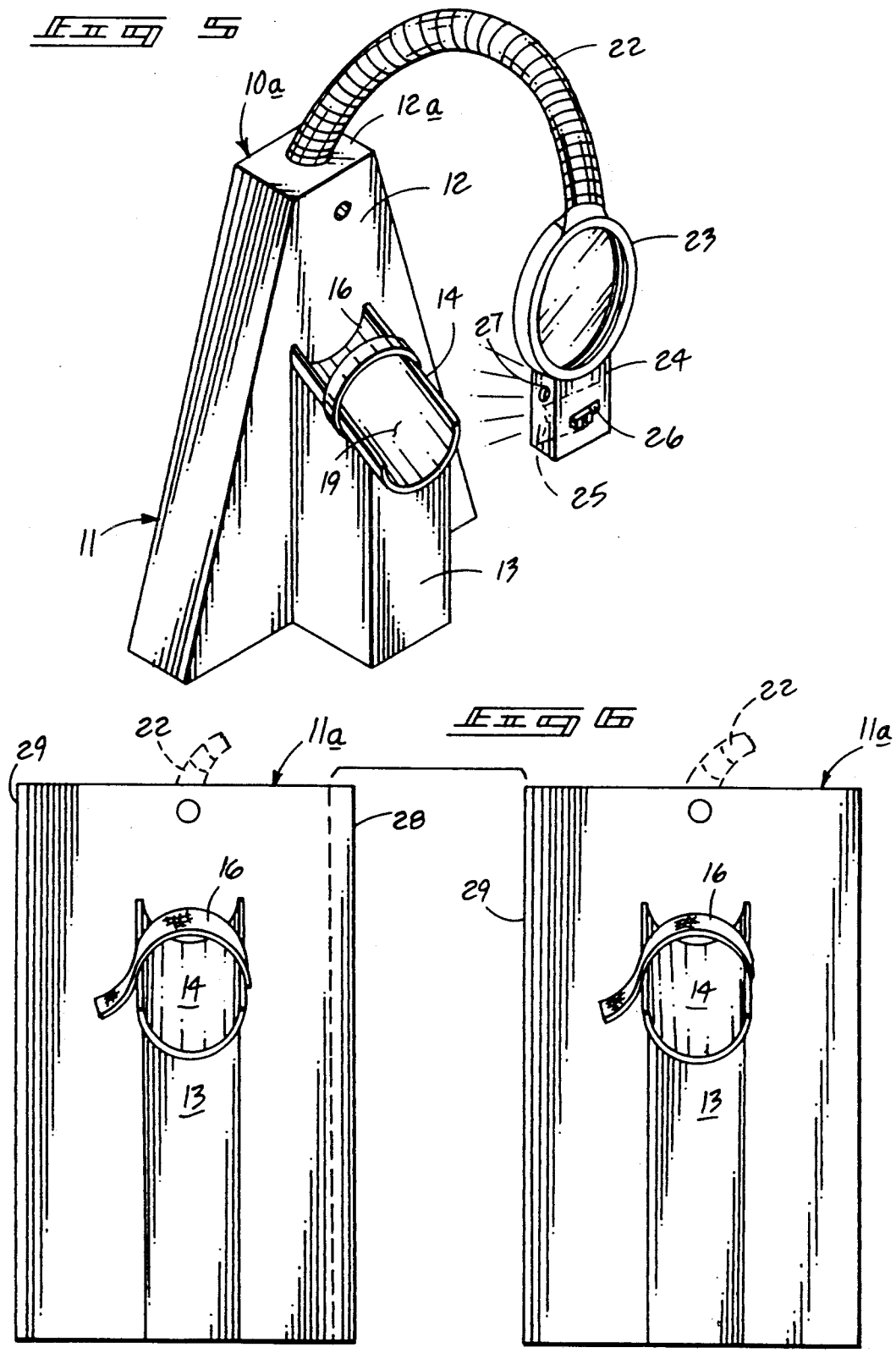

SYRINGE BOTTLE SUPPORT APPARATUS

BACKGROUND OF THE INVENTION

1. Field of the Invention

The field of invention relates to syringe bottle support apparatus, and more particularly pertains to a new and improved syringe bottle support apparatus wherein the same fixedly secures and orients the syringe bottle in an inclined downward orientation to permit filling of an associated syringe therefrom.

2. Description of the Prior Art

Individuals with diminished physical capacity are frequently at odds with a syringe in attempting to fill the syringe from an associated chemical container to provide steady support of the container during a filling procedure. The instant invention attempts to overcome deficiencies of the prior art by providing a structure permitting the selective filling of the syringe in a convenient and readily accessible manner. Examples of the prior art include U.S. Pat. No. 3,762,673 to Koslovsky wherein a medical unit includes a clip member and a snap-cap to secure and insulin bottle thereto, with a syringe support and alcohol sponge container mounted on the unit.

U.S. Pat. No. 2,201,257 to Bell sets forth a nursing bottle support, wherein the support includes an aperture and a cylindrical sleeve mounted within the aperture to frictionally secure a nursing bottle therewithin.

U.S. Pat. No. 2,028,694 to Spinks sets forth a holder assembly including a plurality of slots for mounting various components in a vertical orientation, including a medially positioned cylindrical clip for mounting a fluid container therewithin.

U.S. Pat. No. 2,899,153 to Parker sets forth a receptacle rest wherein a plate includes a plurality of upstanding spring ears to frictionally clamp and secure the container therewithin.

U.S. Pat. No. 4,001,444 to Clarke sets forth a baby food feeder, wherein a cylindrical clip mount secures a baby bottle in an upwardly tipped angular orientation relative to an underlying support.

As such, it may be appreciated that there continues to be a need for a new and improved syringe bottle support apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of syringe bottle support apparatus now present in the prior art, the present invention provides a syringe bottle support apparatus wherein the same fixedly orients a chemical syringe bottle container in a downwardly oriented fixed orientation for permitting access thereto by a syringe. As such, the general purpose of the present invention, which will be described subsequently in greater detail, is to provide a new and improved syringe bottle support apparatus which has all the advantages of the prior art syringe bottle support apparatus and none of the disadvantages.

To attain this, the present invention provides an apparatus arranged to fixedly mount a syringe bottle in a downwardly angulated orientation, including a support member formed with a concave semi-cylindrical sleeve, with the sleeve mounting an elastomeric band selectively securable to a side of t the sleeve for assembly of the bottle to the sleeve to permit access of the bottle in filling of a syringe therefrom. A modification of the invention includes illumination structure to enhance visibility of the organization in use.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Futher, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved syringe bottle support apparatus which has all the advantages of the prior art syringe bottle support apparatus and none of the disadvantages.

It is another object of the present invention to provide a new and improved syringe bottle support apparatus which may be easily and efficiently manufactured and marketed.

It is a further object of the present invention to provide a new and improved syringe bottle support apparatus which is of a durable and reliable construction.

An even further object of the present invention is to provide a new and improved syringe bottle support apparatus which is susceptible of a low cost of manufacture with regard to both materials and labor, and which accordingly is then susceptible of low prices of sale to the consuming public, thereby making such syringe bottle support apparatus economically available to the buying public.

Still yet another object of the present invention is to provide a new and improved syringe bottle support apparatus which provides in the apparatuses and methods of the prior art some of the advantages thereof, while simultaneously overcoming some of the disadvantages normally associated therewith.

Still another object of the present invention is to provide a new and improved syringe bottle support apparatus wherein the same fixedly mounts a syringe in a downwardly oriented inclination to permit filling of a syringe therefrom eliminating need for manual support of the bottle or container.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of a prior art medial unit supporting an insulin container.

FIG. 2 is an orthographic frontal view, taken in elevation, of the instant invention.

FIG. 3 is an orthographic side view, taken in elevation, of the instant invention.

FIG. 4 is an isometric illustration of the instant invention.

FIG. 5 is an isometric illustration of a modification of the instant invention.

FIG. 6 is an orthographic frontal view, taken in elevation, of modified support bases permitting assemblage of the plurality of bases.

DESCRIPTION OF THE PREFERRED EMBODIMENT

Figure 7:
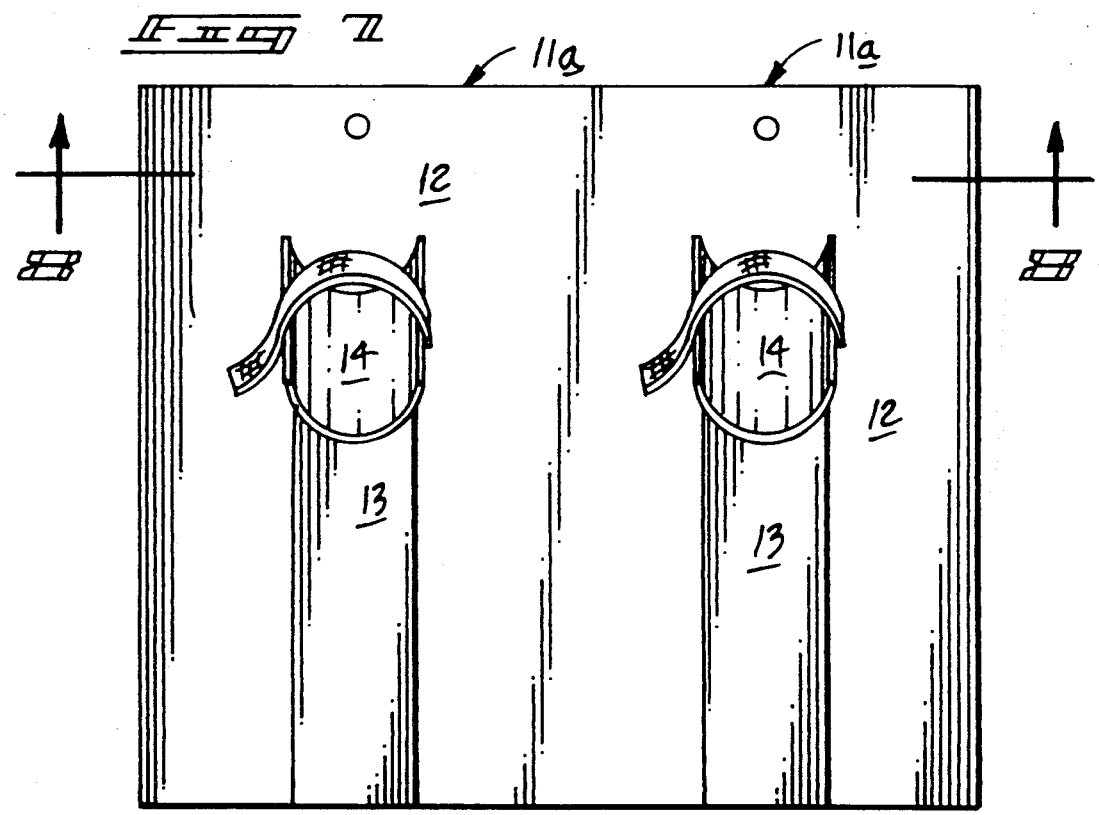
FIG. 7 is an orthographic frontal view, taken in elevation, of the bases of FIG. 6 in an assembled orientation.
Figure 8:
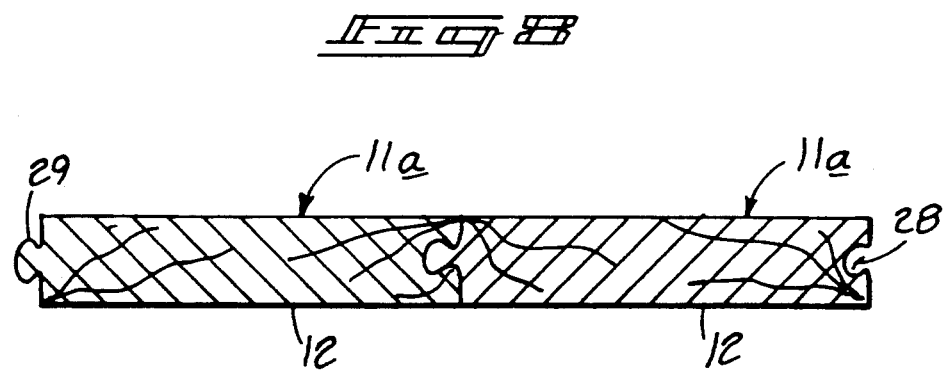
FIG. 8 is an orthographic view, taken along the lines 8—8 of FIG. 7, in the direction indicated by the arrows.

With reference now to the drawings, and in particular to FIGS. 1 to 8 thereof, a new and improved syringe bottle support apparatus embodying the principles and concepts of the present invention and generally designated by the reference numeral 10 will be described.

FIG. 1 illustrates a prior art medical unit 1, wherein a cylindrical spring clip member 2 mounts an insulin containing bottle thereto, with an alcohol sponge container 3 and a syringe support cradle 4 mounted on a single base of the organization 1, in a manner as set forth in U.S. Pat. No. 3,762,673.

More specifically, the syringe bottle support apparatus 10 of the instant invention essentially comprises an elongate support base 11 defined by a first height vertically mounted and including a forward vertical base wall 12 and a horizontal top wall 12a. A second support base 13 defined by a second height less than the first height extends from a lower terminal end of the forward vertical base wall 12 upwardly and extending below the horizontal top wall 12a. The second support base 13 mounts a semi-cylindrical sleeve 14 at an upper terminal end thereof, with a semi-cylindrical sleeve 14 inclined downwardly relative to the first and second support bases 11 and 12 respectively, and defining an acute included angle 15 (see FIG. 3) between the sleeve 14 and the vertical wall 12. A strap 16 is mounted to overlie the sleeve 14 and is fixedly mounted to one side of the sleeve 14 and removably mounted to a second side of the sleeve 14 diametrically opposed to the first side to permit the strap 16 to overlie a concave trough 19 defined by the sleeve 14. A first hook and loop fastener patch 17 is accordingly mounted on an interior surface of a free end of the strap 16 adjacent the second side of the sleeve 14, with a second hook and loop fastener path 18 cooperative with the first hook and loop fastener patch, wherein the second hook and loop fastener patch 18 is fixedly mounted to the second side of the sleeve 14 in a manner as illustrated in FIG. 3 for example.

FIG. 4 illustrates the mounting of a chemical container dispenser 20 on the sleeve 14 within the trough 19, with the container dispenser cap 20a oriented downwardly relative to the bottom end of the container 20. In this manner, a syringe 21 is provided access to the cap 20a for extraction of a chemical therefrom for medical use.

FIG. 5 illustrates the use of the organization, with an adjustably mounted deformably positionable support arm 22 mounted at its lower terminal end to the horizontal to wall 12a, with a magnification lens and housing 23 mounted to a forward terminal end of the support arm 22. The support arm 22 is radially directed and fixedly mounted to the lens and housing 23, as illustrated in FIG. 5. The magnification lens and housing 23 further include a light housing 24, with a light member 25 mounted to a rear surface thereof to direct light onto the concave trough 19 to enhance visibility thereof in cooperation with the magnification lens mounted within the housing of the magnification lens and housing organization 23 to enhance visible observation of positioning of the syringe 21 through the cap 20a. A switch 26 effects selective illumination of the light member 25 and operates through a conventional battery 27 mounted within the housing to effect such illumination.

FIG. 6 illustrates the use of the first support base 11, including a vertical first side wall 28 containing a groove coextensively therewith and a parallel vertical second side wall 29 that defines a tongue member that is complementarily received within the groove 28 to permit side-by-side securement of a plurality of modified first support bases 11a, in a manner as illustrated in FIG. 7, in association with the support arms and associated magnification and illumination structure as set forth above.

As to the manner of usage and operation of the instant invention, the same should be apparent from the above disclosure, and accordingly no further discussion relative to the manner of usage and operation of the instant invention shall be provided With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A syringe bottle support apparatus comprising, in combination,
    a first support base, the first support base defined by a first height and including a first support base forward vertical wall, and
    a first support base horizontal top wall, and
    a second support base defined by a second height less than the first height extending from a lower terminal end of the first support base and fixedly mounted to the first support base vertical wall and extending below the horizontal top wall, and
    the second support base mounting a sleeve at an upper terminal end of the second support base, and
    strap means mounted to the sleeve for securement of a chemical dispensing container to the sleeve, and
    wherein the sleeve is of a semi-cylindrical configuration and fixedly mounted to the upper terminal end of the second support base, and the sleeve coextensively mounted to the upper terminal end of the second support base and extending forwardly thereof and extending downwardly relative to the first support base vertical wall, and defining an acute included angle between the sleeve and the first support base vertical wall, and
    wherein the strap means is formed of elastomeric material and is fixedly mounted to a first side of the sleeve, wherein the strap is selectively and reasonably securable to a second side of the sleeve, wherein the second side of the sleeve includes a second hook and loop fastener patch, and the strap includes a first hook and loop fastener patch selectively cooperative with the second hook and loop fastener patch, with the first hook and loop fastener patch mounted to a free end of the strap remote from the first side of the sleeve, with the strap oriented to overlie the sleeve, and the sleeve defining a concave trough to receive the container therewithin, and
    further including an adjustably mounted deformably positionable support arm fixedly mounted at its lower terminal end to the horizontal top wall, and a forward end of the supprt arm spaced from the horizontal top wall is radially and fixedly mounted to a magnification lens housing, including a magnification lens therewithin, and the housing including a light housing mounted to the magnification lens, with a light member mounted within the light housing positioned below the magnification lens, with a switch mounted within the light housing to selectively actuate the light member.

2. An apparatus as set forth in claim 1 wherein the first support base includes a vertical first side wall spaced from and parallel to a vertical second side wall, the first side wall includes an elongate coextensive groove and the vertical second side wall includes an elongate tongue member to permit securement of a further first support base, with the further first support base including a vertical first side wall and a vertical second side wall, with the vertical second side wall of the further support base receivable within the vertical first side wall of the first support base.

* * * * *